United States Patent
Stephenson et al.

(10) Patent No.: US 10,500,751 B2
(45) Date of Patent: Dec. 10, 2019

(54) BLADE-PROTECTING SHEATH FOR AN ULTRASONIC CUTTING SYSTEM

(71) Applicant: THE BOEING COMPANY, Chicago, IL (US)

(72) Inventors: Benjamin J. Stephenson, Seattle, WA (US); Scott K. Frankenbery, Tacoma, WA (US); Robert L. Anderson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 123 days.

(21) Appl. No.: 15/264,050

(22) Filed: Sep. 13, 2016

(65) Prior Publication Data

US 2018/0070973 A1    Mar. 15, 2018

(51) Int. Cl.
*B26D 7/08* (2006.01)
*B26D 7/00* (2006.01)
*A61B 17/32* (2006.01)
*A61B 90/00* (2016.01)

(52) U.S. Cl.
CPC ............... *B26D 7/086* (2013.01); *B26D 7/00* (2013.01); *A61B 17/320068* (2013.01); *A61B 2090/0801* (2016.02)

(58) Field of Classification Search
CPC ............ A61B 90/03; A61B 17/320068; A61B 17/3215; A61B 17/3217; A61B 2090/08021; A61B 2090/0801; A61B 2017/32113; A61B 2050/21; A61B 50/3001; A61B 50/362; A61B 17/32; A61B 2017/320072; A61B 2017/320074; B26B 29/00; B26B 29/02; B26B 29/025; B26B 29/04

See application file for complete search history.

(56) References Cited

U.S. PATENT DOCUMENTS

| | | | | |
|---|---|---|---|---|
| 5,057,119 A * | 10/1991 | Clark | ............... | A61B 17/3215 464/37 |
| 5,059,210 A | 10/1991 | Clark | | |
| 2010/0186556 A1* | 7/2010 | Lin | ............... | B25B 13/06 81/125 |
| 2016/0193723 A1* | 7/2016 | Su | ............... | B25B 13/06 81/438 |
| 2017/0074308 A1* | 3/2017 | Tseng | ............... | B25B 23/0035 |

* cited by examiner

*Primary Examiner* — Diane D Yabut
*Assistant Examiner* — Majid Jamialahmadi
(74) *Attorney, Agent, or Firm* — Joseph M. Butscher; The Small Patent Law Group, LLC

(57) ABSTRACT

A blade-protecting sheath is configured to protect a cutting blade of an ultrasonic cutting system. The blade-protecting sheath includes a main body having a first end and an opposite second end, a blade-receiving channel formed through the first end, and a nut-retention chamber connected to the blade-receiving channel. The nut-retention chamber is defined by interior planar walls that are configured to receive and constrain a nut of the ultrasonic cutting system. A blade slot is connected to the nut-retention chamber. The cutting blade is configured to pass into the blade slot and be secured within a blade chamber.

19 Claims, 5 Drawing Sheets

BLADE-PROTECTING SHEATH FOR AN ULTRASONIC CUTTING SYSTEM

FIELD OF THE DISCLOSURE

Embodiments of the present disclosure generally relate to protective systems for a cutting blade of an ultrasonic cutting system.

BACKGROUND OF THE DISCLOSURE

Ultrasonic cutting systems are used in various industries for a wide variety of purposes. For example, ultrasonic cutting systems are used in aerospace and textile industries to provide precise cuts of composite components, textiles, thermoplastics, elastomeric materials, and the like.

A typical ultrasonic cutting system includes a power horn operatively connected to a cutting blade through a nut. The power horn is connected to a power source, such as a battery, power outlet (such as through a cord and plug), and/or the like. The nut secures the cutting blade to the power horn. In order to securely install or remove the cutting blade from the power horn, the nut is tightened or loosened, respectively.

However, during installation and removal, the cutting blade is typically exposed. Therefore, if an operator loses grip, slips, or the like during such times, the exposed cutting blade may contact the operator. Because the cutting blade is typically extremely sharp, the contact of the cutting blade may cut the operator. Further, during installation and removal, the sharp cutting blades may also be damaged, such as by being inadvertently dropped.

SUMMARY OF THE DISCLOSURE

A need exists for a system for protecting a cutting blade of an ultrasonic cutting system when not in use. A need exists for a system for safely installing and removing a cutting blade of an ultrasonic cutting system.

With those needs in mind, certain embodiments of the present disclosure provide a blade-protecting sheath that is configured to protect a cutting blade of an ultrasonic cutting system. The blade-protecting sheath includes a main body having a first end and an opposite second end. A blade-receiving channel is formed through the first end. A nut-retention chamber is connected to the blade-receiving channel. The nut-retention chamber is defined by interior planar walls that are configured to receive and constrain a nut of the ultrasonic cutting system. A blade slot is connected to the nut-retention chamber. The cutting blade is configured to pass into the blade slot and be secured within a blade chamber.

In at least one embodiment, the blade-protecting sheath includes opposed barrier blocks within the main body. The blade slot is defined between the opposed barrier blocks. The blade slot has a clearance height that is greater than a depth of the cutting blade. In at least one embodiment, the blade chamber is longer, wider, and deeper than the cutting blade. The main body is configured to suspend the cutting blade within the blade chamber. In at least one embodiment, no portion of the cutting blade directly contacts any portion of the blade-protecting sheath when the cutting blade is secured within the blade chamber.

The blade-protecting sheath includes at least one magnet that is configured to magnetically couple the main body to the nut.

At least a portion of the main body may include an outer perimeter that is complementary to an operative portion of a tool. The operative portion of the tool is configured to conform to the hexagonal outer perimeter. The outer perimeter may be hexagonally shaped. In at least one embodiment, the outer perimeter includes one or both of the first end or the second end.

The blade-protecting sheath may include at least one ergonomic recess formed in the main body. The ergonomic recess is configured to be gripped and grasped by an individual. The ergonomic recess may include an inwardly-bowed arcuate surface. The ergonomic recess may include an outer textured surface.

Certain embodiments of the present disclosure provide a protective system that includes an ultrasonic cutting system including a power horn coupled to a cutting blade through a nut. A blade-protecting sheath protects the cutting blade when the ultrasonic cutting system is not in use and when the cutting blade is removed from the power horn.

DETAILED DESCRIPTION OF THE DISCLOSURE

Figure 1:
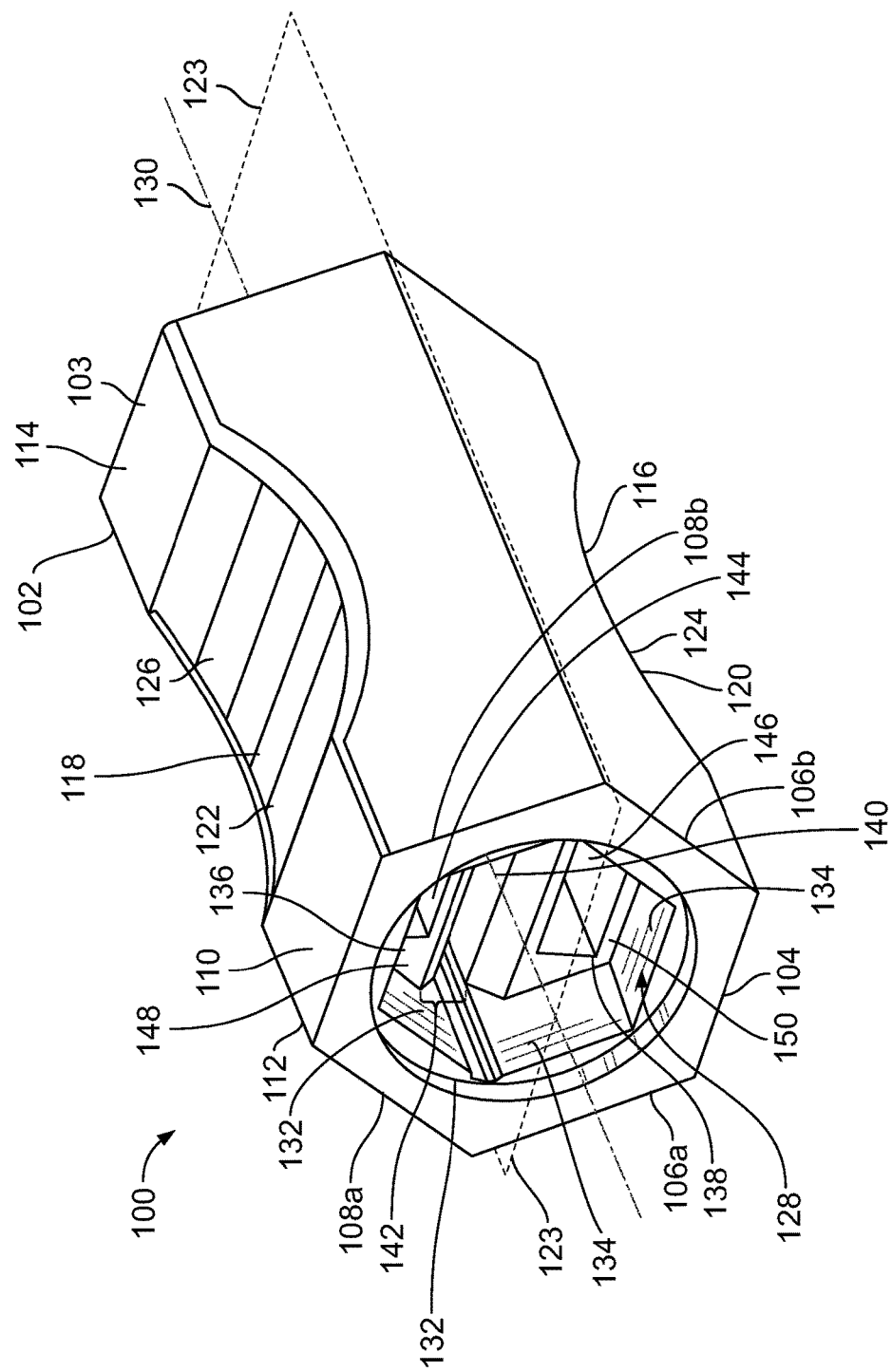
FIG. 1 illustrates a perspective view of a blade-protecting sheath, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a blade-protecting sheath for an ultrasonic cutting system. A cutting blade of an ultrasonic cutting system is formed of carbide, which is a non-magnetic material. In contrast, a nut that is used to secure the cutting blade to a power horn of an ultrasonic cutting system is formed of a magnetic material. The blade-protecting sheath includes one or more magnets that are configured to magnetically couple the blade-protecting sheath to the nut, while covering the cutting blade, thereby ensuring that the blade-protecting sheath is securely held in place. Because the cutting blade is formed of a non-magnetic material, the magnet does not magnetically couple to the cutting blade.

In at least one embodiment, an outer surface of the blade-protecting sheath is hexagonally shaped (such as a ¾ inch hexagonal shape), which is complementary to a tool (such as a socket wrench) that is used to engage the blade-protecting sheath during an installation and/or removal process with respect to a power horn. The outer perimeter hexagonal pattern shape of the blade-protecting sheath is configured to be engaged by an operative portion of a tool, and allow for torque application during assembly or removal of the cutting blade with respect to the power horn. As such, the cutting blade may be installed and removed without being exposed to an operator, while also being protected from damage by the blade-protecting sheath. In at least one embodiment, at least a portion of an outer surface of the blade-protecting sheath includes a textured groove, such as in a middle portion, to provide an ergonomic grip that is configured to be engaged by an operator during installation and removal.

When positioned over the nut of the ultrasonic cutting system, the blade-protecting sheath provides a shock absorber in relation to the cutting blade. As such, if the blade-protecting sheath covering the cutting blade is dropped, forces exerted into the blade-protecting sheath are transmitted into the blade-protecting sheath around the cutting blade (in contrast to be exerted into the cutting blade), thereby preventing, minimizing, or otherwise reducing a risk of damage to the cutting blade. Further, each blade-protecting sheath may be a bright, bold, or luminescent color that is selected to be readily noticeable and distinguishable from cutting blades and/or other portions of an ultrasonic cutting system.

The blade-protecting sheath may be molded, machined, printed, or similarly produced. In at least one embodiment, the blade-protecting sheath is formed via three-dimensional (3D) printing as a unitary piece of plastic. The 3D printing provides an efficient and effective process of forming the blade-protecting sheath.

FIG. 1 illustrates a perspective view of a blade-protecting sheath 100, according to an embodiment of the present disclosure. The blade-protecting sheath 100 is formed as a single, unitary piece, such as formed of plastic or non-ferrous metal. In at least one embodiment, the blade-protecting sheath 100 is formed as a single, unitary piece of plastic through 3D printing, which provides an efficient and effective process of forming the blade-protecting sheath 100. Alternatively, the blade-protecting sheath 100 may be formed through various other processes, such as through injection molding, machining, and/or the like.

The blade-protecting sheath 100 includes a main body 102 having an outer surface 103 that includes a wall 104 connected to a pair of outwardly-angled walls 106*a* and 106*b*, which, in turn, connect to inwardly-angled walls 108*a* and 108*b*, which, in turn, connect a wall 110. The walls 104 and 110 at ends 112 and 114 are parallel to one another. Similarly, the walls 106*a* and 108*b* at the ends 112 and 114 are generally parallel to one another. Further, the walls 106*b* and 108*a* are generally parallel to one another. As such, the outer perimeter of the blade-protecting sheath 100 is generally hexagonally shaped, at least at the ends 112 and 114.

The hexagonal outer shape of the main body 102 is complementary to a tool, such as a socket wrench (for example, a ¾ inch hexagonal socket of a socket wrench). In this manner, the hexagonal socket of the socket wrench is configured to securely fit over the blade-protecting sheath 100 at either end 112 or 114. Because of the conforming shape, the main body 102 may be rotationally constrained by the hexagonal socket, when the socket is secured over the first end 112 and/or the second end 114.

As shown, the ends 112 and 114 may be the same size. Neither end 112 or 114 tapers to a point or apex. In at least one embodiment, both ends 112 and 114 are configured to be securely engaged by a tool (such as a socket wrench). For example, a socket of a socket wrench may be positioned over the length of the main body 102 from the end 112 to the end 114.

Alternatively, the outer surface 103 may be shaped and sized differently. For example, the outer surface 103 may have a square, circular, octagonal, or other such shape.

Ergonomic recesses 116 and 118 are formed in the walls 104, 106*a*, 106*b* and 110, 108*a*, and 108*b* between the ends 112 and 114. As shown, the recesses 116 and 118 are generally centered with respect to the respective walls 104 and 110. The recesses 116 and 118 may be mirror image shapes with respect to one another.

The recesses 116 and 118 include arcuate surfaces 120 and 122 that inwardly-bow towards a central horizontal plane 122 of the blade-protecting sheath 100. Each recess 116 and 118 may include a constant radius of curvature over a length thereof. Optionally, the radius of curvature may differ over a length of each recess 116 and 118.

The recesses 116 and 118 provide ergonomic features that are configured to be grasped by an individual. In particular, the recesses 116 and 118 are sized and shaped to be firmly grasped by fingers and/or thumbs of an individual. In at least one embodiment, the recesses 116 and 118 also include outer textured surfaces 124 and 126 (such as ribs, ridges, embossments, dimples, and/or the like) that are configured to allow an individual to firmly grip and grasp the recesses 116 and 118.

More or less ergonomic recesses 116 and 118 than shown may be used. For example, the blade-protecting sheath 100 may include only one recess 116 and 118. Optionally, the blade-protecting sheath 100 may include additional recesses. Further, the recesses 116 and 118 may be provided at one or both ends 112 or 114, or may otherwise not be centered with respect to the blade-protecting sheath 100. Alternatively, the blade-protecting sheath 100 may not include the ergonomic recesses 116 and 118.

A blade-receiving channel 128 is formed through the end 122 and is generally coaxial with a longitudinal axis 130 of the blade-protecting sheath 100. The blade-receiving channel 128 provides a circular, hexagonal, or other shaped inlet defined between the walls 104, 106*a*, 106*b*, 108*a*, 108*b*, and 110 that connects and leads into a nut-retention chamber 132 defined between interior planar walls 134 defining a hexagonal pattern. The interior planar walls 134 provide a complementary shape to a nut (not shown in FIG. 1) of an ultrasonic cutting system (not shown in FIG. 1) and are configured to securely fit around the nut. The nut-retention chamber 132 is defined by interior planar walls 134 and configured to receive and rotationally constrain a nut of the ultrasonic cutting system. Alternatively, the interior planar walls 134 may be shaped differently to be complementary to a nut having a different shape.

The nut-retention chamber 132 extends to interior opposed barrier blocks 136 and 138 separated by a blade slot 140. The barrier blocks 136 and 138 may extend along a length of the blade-protecting sheath 100 to the end 114, which may be closed. The blade slot 140 has a clearance height 142 that is greater than a depth of a cutting blade (not shown in FIG. 1). As such, when the blade is inserted into the blade slot 140 between the barrier blocks 136 and 138, the blade does not abut into either the barrier blocks 136 and 138.

Magnet channels 144 and 146 are formed in proximal ends 148 and 150 of the barrier blocks 136 and 138, respectively. The magnet channels 144 and 146 are configured to receive and retain magnets (not shown in FIG. 1). Because the cutting blade of the ultrasonic cutting system is formed of carbide, the magnets do not magnetically couple to the cutting blade. Instead, the magnets magnetically and securely couple the blade-protecting sheath 100 to the nut.

Figure 2:
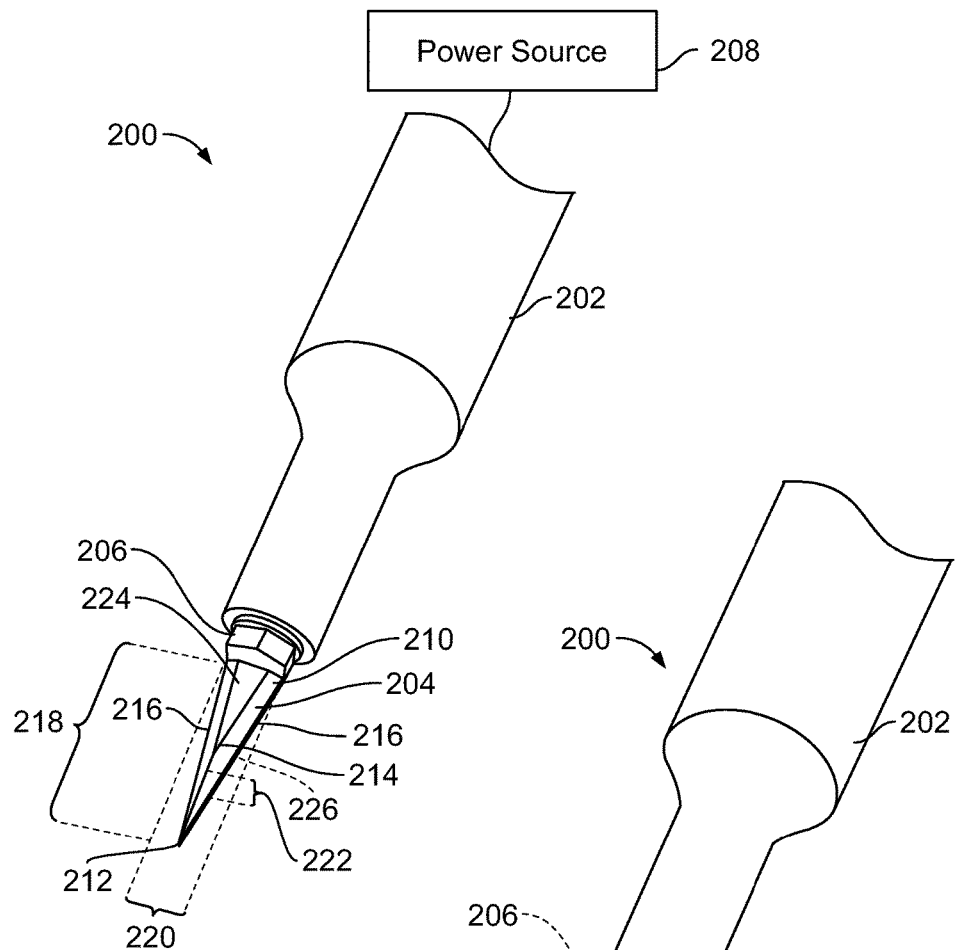
FIG. 2 illustrates a perspective view of an ultrasonic cutting system, according to an embodiment of the present disclosure.

FIG. 2 illustrates a perspective view of an ultrasonic cutting system 200, according to an embodiment of the present disclosure. The ultrasonic cutting system 200 includes a power horn 202 coupled to a cutting blade 204 through a nut 206. A power source 208 (such as a battery, plug connected to an external power source, and/or the like) supplies power to the power horn 202. When activated, the power horn 202 ultrasonically excites the cutting blade 204.

The cutting blade 204 includes a base 210 proximate to the nut 206 that connects to a tip 212 through a body 214. The tip 212 and lateral edges 216 of the body are sharp. The cutting blade 204 has a length 218 extending from the base 210 to the tip 212, a width 220 between the lateral edges 216, and a depth 222 between a front surface 224 and an opposite rear surface 226. As shown, the cutting blade 204 is shaped as a triangle or arrowhead. Optionally, the cutting blade 204 may be sized and shaped differently than shown.

Figure 3:
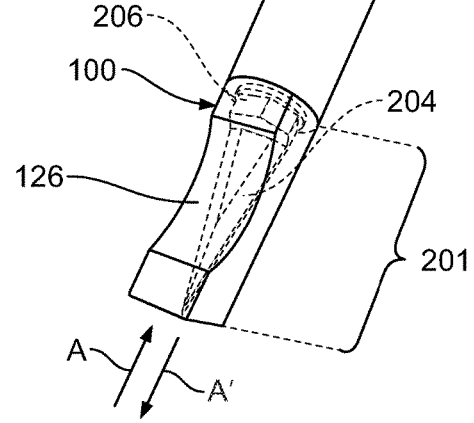
FIG. 3 illustrates a perspective view of a blade-protecting sheath secured to an ultrasonic cutting system over and around a cutting blade and a nut, according to an embodiment of the present disclosure.

FIG. 3 illustrates a perspective view of the blade-protecting sheath 100 secured to the ultrasonic cutting system 200 over and around the cutting blade 204 (shown in FIG. 2) and the nut 206 (shown in FIG. 2), according to an embodiment of the present disclosure. The blade-protecting sheath 100 coupled to the ultrasonic cutting system 200 provides a protective system 201 that protects the cutting blade 204 (shown in FIG. 2) from being damaged, and from inadvertently cutting an object or an individual. Referring to FIGS. 1-3, when the ultrasonic cutting system 200 is not in use and/or when the cutting blade 204 is removed from the power horn 202, the blade-protecting sheath 100 is secured over the cutting blade 204 to protect the cutting blade 204 from being damaged, or inadvertently cutting an object and/or individual.

In order to secure the blade-protecting sheath 100 to the ultrasonic cutting system 200, the blade-receiving channel 128 is oriented toward the tip 212 of the cutting blade 204. The blade-protecting sheath 100 is axially aligned with the cutting blade 204 so that the plane(s) in which the blade slot 140 resides are parallel with the plane(s) in which the cutting blade 204 resides. The blade-protecting sheath 100 is then urged over the cutting blade 204 in the direction of arrow A, so that the cutting blade 204 passes into the blade slot 140. Continued motion in the direction of arrow A is halted by the end 112 of the main body 102 abutting into the power horn 202 and the barrier blocks 136 and 138 abutting into an end surface of the nut 206, which causes the cutting blade 204 to be suspended within a blade chamber, as described below.

As the blade-protecting sheath 100 is positioned over the cutting blade 204, the interior planar walls 134 (which conform to and are complementary to the outer perimeter of the nut 206) slide thereover, and automatically index and guide the cutting blade 204 into the blade slot 140 between the opposed barrier blocks 136 and 138. Because the blade slot 140 has a clearance height 142 that is greater than the depth 222 of the cutting blade 204, the barrier blocks 136 and 138 do not contact the cutting blade 204. In general, the blade slot 140 is an inlet end of a blade chamber 302 that is longer, wider, and deeper than the cutting blade 204. As such, when the cutting blade 204 is retained within the blade chamber 302, the cutting blade 204 does not directly contact any portion of the blade-protecting sheath 100. Instead, the cutting blade 204 is securely suspended within the blade chamber 302 between interior wall portions of the blade-protecting sheath 100. Therefore, forces transmitted into the blade-protecting sheath 100 are not transmitted into the cutting blade 204, which protects the cutting blade 204 from damage. Instead, any force exerted into the blade-protecting sheath 100 is dampened or otherwise reduced by the blade-protecting sheath 100, and/or transmitted into the nut 206.

The magnets retained within the magnet channels 144 and 146 magnetically couple the blade-protecting sheath 100 to the nut 206, thereby securely connecting the blade-protecting sheath 100 to the ultrasonic cutting system 200. The magnetic coupling prevents the blade-protecting sheath 100 from inadvertently dislodging from the ultrasonic cutting system 200. In order to remove the blade-protecting sheath 100 from the ultrasonic cutting system 200, an individual grasps the blade-protecting sheath 100 (such as by the ergonomic recesses 126), and pulls the blade-protecting sheath 100 away from the ultrasonic cutting system 200 in the direction of arrow A' with sufficient force to overcome the magnetic coupling force of the magnets with respect to the nut 206.

Figure 4:
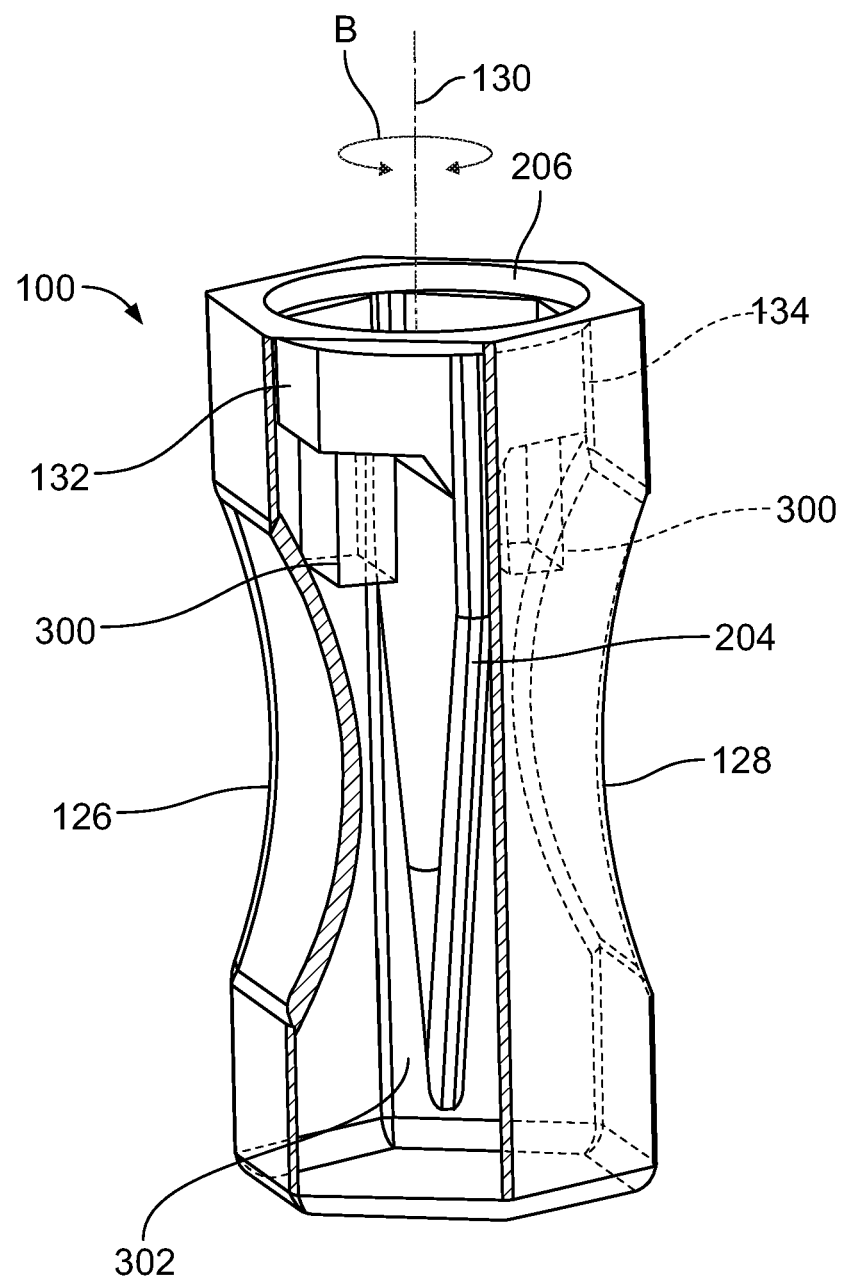
FIG. 4 illustrates a perspective internal view of a blade-protecting sheath protecting a cutting blade, according to an embodiment of the present disclosure.

FIG. 4 illustrates a perspective internal view of the blade-protecting sheath 100 protecting the cutting blade 204, according to an embodiment of the present disclosure. As shown, interior planar walls 134 of the nut-retention chamber 132 conform around the nut 206, thereby rotationally constraining the nut 206. As such, any rotational motion of the blade-protecting sheath 100 about the longitudinal axis 130 in the direction of arcs B causes a corresponding rotational motion of the nut 206 and the cutting blade 204.

Magnets 300 are retained within the magnet channels 144 and 146 (shown in FIG. 1) and magnetically couple the blade-protecting sheath 100 to the nut 206. As shown, the nut 206 and the cutting blade 204 are removed from the power horn 202 (shown in FIGS. 2 and 3). In this manner, the blade-protecting sheath 100 may be used to protect the cutting blade 204 from damage and/or cutting objects or individuals as the cutting blade 204 is stored and/or transported between uses. The blade chamber 302 is longer, wider, and deeper than the cutting blade 204. The cutting blade 204 is retained within the blade chamber 302 without directly contacting any portion of the blade-protecting sheath 100. As shown, the cutting blade 204 is securely suspended within the blade chamber 302 between interior wall portions of the blade-protecting sheath 100.

If the blade-protecting sheath 100 is dropped, bumped, or otherwise subjected to a force, the force is blunted and dampened by the blade-protecting sheath 100. Most, if not all, of any residual force is transmitted from the blade-protecting sheath 100 into the nut 206, but not the cutting blade 204, which is suspended within the blade chamber 302.

Figure 5:
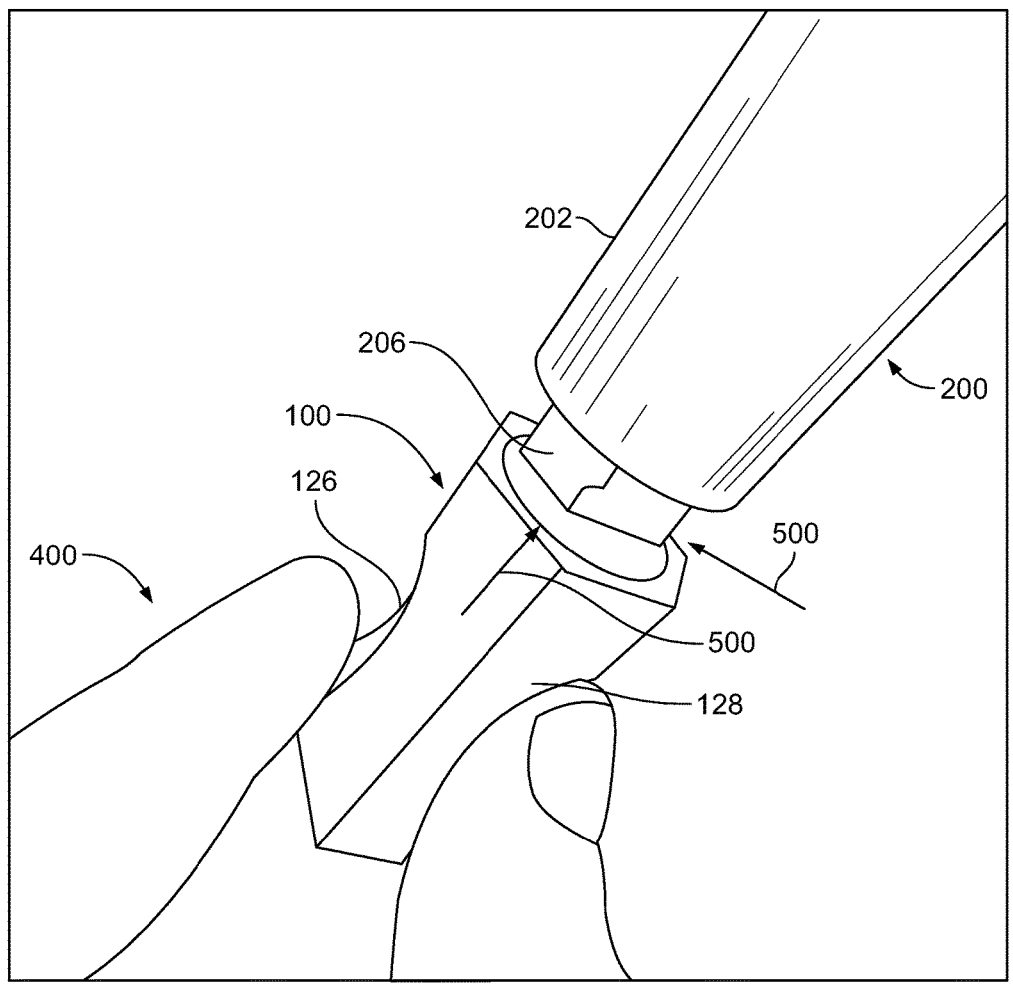
FIG. 5 illustrates a perspective view of a blade-protecting sheath being grasped by an individual, according to an embodiment of the present disclosure.

FIG. 5 illustrates a perspective view of the blade-protecting sheath 100 being grasped by an individual 400, according to an embodiment of the present disclosure. The ergonomic recesses 126 and 128 provide grippable surfaces that are configured to be gripped and grasped by the individual.

As noted above, forces 500 exerted into the blade-protecting sheath 100 are transmitted into the nut 206, instead of the cutting blade 204 (shown in FIG. 4), which is suspended within the blade chamber 302 (shown in FIG. 4).

Figure 6:
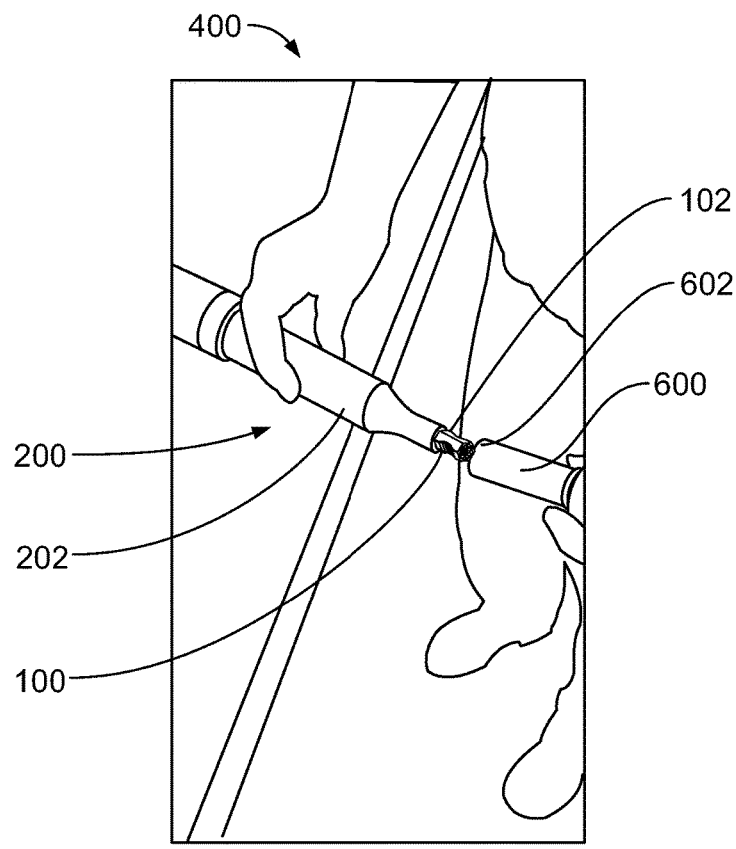
FIG. 6 illustrates a perspective view of a tool engaging a blade-protecting sheath covering a cutting blade, according to an embodiment of the present disclosure.

FIG. 6 illustrates a perspective view of a tool 600 engaging the blade-protecting sheath 100 covering a cutting blade 204 (shown in FIG. 4), according to an embodiment of the present disclosure. The blade-protecting sheath 100 is securely positioned over and around the cutting blade 204, as shown and described with respect to FIGS. 3 and 4. The tool 600 may be a socket wrench having an operative portion, such as a distal socket 602, which fits over the main body 102 of the blade-protecting sheath 100. Referring to FIGS. 1 and 6, as described above with respect to FIG. 1, the outer shape of at least the ends 112 and 114 of the main body 102 are complementary to an inner shape of the socket 602. The inner shape of the socket 602 conforms to an outer shape of the at least the ends 112 and 114. Therefore, the tool 600 may be used to torque the blade-protecting sheath 100, and therefore the cutting blade 204 and nut 206, into a secure position or a disconnected position. The tool 600 may be used to securely tighten the cutting blade 204 to the power horn 202. The tool 600 may be used to provide an initial disconnection torque of the cutting blade 204 with respect to the power horn 202, after which the individual 400 may grasp the blade-protecting sheath 100 and disconnect the blade-protecting sheath 100, which retains the cutting blade 204, by hand.

When the blade-protecting sheath 100 is coupled to the nut 206, as described above, the individual 400 may use the blade-protecting sheath 100 to tighten and/or the loosen the cutting blade 204 with respect to the power horn 202. Because the nut-retention chamber 132 conforms to the outer surface of the nut 206, rotational motion of the blade-protecting sheath 100 causes a corresponding motion in the nut 206 and the cutting blade 204. In this manner, the blade-protecting sheath 100 may be used to connect and disconnect the cutting blade 204 from the power horn 202, while at the same time protecting the individual 400 from being cut by the cutting blade 204.

Figure 7:
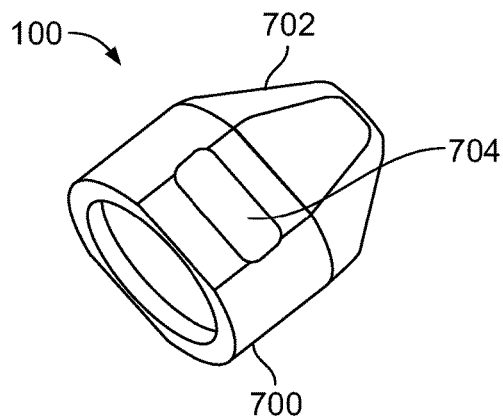
FIG. 7 illustrates a perspective view of a blade-protecting sheath, according to an embodiment of the present disclosure.

FIG. 7 illustrates a perspective view of the blade-protecting sheath 100, according to an embodiment of the present disclosure. The blade-protecting sheath 100 is similar to that described above with respect to FIG. 1, except the embodiment shown in FIG. 7 has a cylindrical base 700 connected to a conic tip 702. The base 700 may include outer textured surfaces 704 that allow an individual to firmly grip the blade-protecting sheath 100. An outer surface of the base 700 may or may not be complementary to a portion of a tool.

Figure 8:
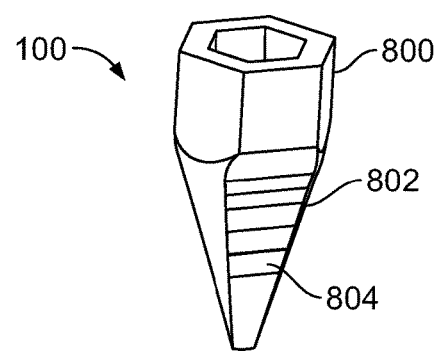
FIG. 8 illustrates a perspective view of a blade-protecting sheath, according to an embodiment of the present disclosure.

FIG. 8 illustrates a perspective view of the blade-protecting sheath 100, according to an embodiment of the present disclosure. The blade-protecting sheath 100 includes a hexagonal base 800 connected to a conic tip 802 that is longer than the conic tip 702, so as to accommodate a longer cutting blade. The conic tip 802 may include outer textured surfaces 804. Referring to FIGS. 1, 7, and 8, the blade-protecting sheath 100 may include various other shapes and sizes, depending on a size and shape of a cutting blade that is to be protected by the blade-protecting sheath 100.

Referring to FIGS. 1-8, embodiments of the present disclosure provide systems for protecting a cutting blade of an ultrasonic cutting system when not in use. Embodiments of the present disclosure provide systems for safely installing and removing a cutting blade of an ultrasonic cutting system.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A protective system comprising:
   an ultrasonic cutting system including a power horn coupled to a cutting blade through a nut; and
   a blade-protecting sheath that protects the cutting blade the blade-protecting sheath comprising:
   a main body having a first end and an opposite second end;
   a blade-receiving channel formed through the first end;
   a nut-retention chamber connected to the blade-receiving channel, wherein the nut-retention chamber is defined by interior planar walls that receive and constrain the nut of the ultrasonic cutting system;

at least one magnet that magnetically couples the main body to the nut; and a blade slot connected to the nut-retention chamber, wherein the cutting blade is configured to pass into the blade slot and be secured within a blade chamber.

2. The protective system of claim 1, wherein the blade-protecting sheath further comprises opposed barrier blocks within the main body, wherein the blade slot is defined between the opposed barrier blocks.

3. The protective system of claim 1, wherein the blade slot has a clearance height that is greater than a depth of the cutting blade.

4. The protective system of claim 1, wherein the blade chamber is longer, wider, and deeper than the cutting blade.

5. The protective system of claim 1, wherein the main body is configured to suspend the cutting blade within the blade chamber.

6. The protective system of claim 1, wherein no portion of the cutting blade directly contacts any portion of the blade-protecting sheath when the cutting blade is secured within the blade chamber.

7. The protective system of claim 1, wherein at least a portion of the main body includes an outer perimeter that is complementary to an operative portion of a tool, wherein the operative portion of the tool is configured to conform to the outer perimeter.

8. The protective system of claim 7, wherein the outer perimeter is hexagonally shaped.

9. The protective system of claim 7, wherein the outer perimeter comprises one or both of the first end or the second end.

10. The protective system of claim 1, wherein the blade-protecting sheath further comprises at least one ergonomic recess formed in the main body, wherein the at least one ergonomic recess is configured to be gripped and grasped by an individual.

11. The protective system of claim 10, wherein the at least one ergonomic recess comprises an inwardly-bowed arcuate surface.

12. The protective system of claim 10, wherein the at least one ergonomic recess includes an outer textured surface.

13. A protective system comprising:

an ultrasonic cutting system including a power horn coupled to a cutting blade through a nut; and a blade-protecting sheath that protects the cutting blade when the ultrasonic cutting system is not in use and when the cutting blade is removed from the power horn, the blade-protecting sheath comprising:

a main body having a first end and an opposite second end;

at least one ergonomic recess formed in the main body, wherein the at least one ergonomic recess is configured to be gripped and grasped by an individual a blade-receiving channel formed through the first end;

a nut-retention chamber connected to the blade-receiving channel, wherein the nut-retention chamber is defined by interior planar walls that receive and constrain the nut of the ultrasonic cutting system;

a blade slot connected to the nut-retention chamber, wherein the cutting blade passes into the blade slot and is secured within a blade chamber, wherein the blade slot has a clearance height that is greater than a depth of the cutting blade, wherein the blade chamber is longer, wider, and deeper than the cutting blade, wherein the cutting blade is suspended within the blade chamber; and at least one magnet that magnetically couples the main body to the nut.

14. The protective system of claim 13, wherein the blade-protecting sheath of further comprises opposed barrier blocks within the main body, wherein the blade slot is defined between the opposed barrier blocks.

15. The protective system of claim 13, wherein no portion of the cutting blade directly contacts any portion of the blade-protecting sheath.

16. The protective system of claim 13, wherein at least one or both of the first end or the second end includes a hexagonally-shaped outer perimeter that is complementary to an operative portion of a tool, wherein the operative portion of the tool is configured to conform to the hexagonal outer perimeter of the at least one or both of the first end or the second end.

17. The protective system of claim 13, wherein the at least one ergonomic recess comprises an inwardly-bowed arcuate surface.

18. The protective system of claim 13, wherein the at least one ergonomic recess includes an outer textured surface.

19. A protective system comprising:

an ultrasonic cutting system including a power horn coupled to a cutting blade through a nut; and a blade-protecting sheath that protects the cutting blade, the blade-protecting sheath comprising:

a main body having a first end and an opposite second end, wherein each of the first end and the second end include a hexagonal outer perimeter that is complementary to an operative portion of a tool, wherein the operative portion of the tool is configured to conform to the hexagonal outer perimeter of each of the first end and the second end;

at least one ergonomic recess formed in the main body, wherein the at least one ergonomic recess is configured to be gripped and grasped by an individual, wherein the at least one ergonomic recess comprises an inwardly-bowed arcuate surface and an outer textured surface;

a blade-receiving channel formed through the first end;

a nut-retention chamber connected to the blade-receiving channel, wherein the nut-retention chamber is defined by interior planar walls that receive and constrain the nut of the ultrasonic cutting system;

at least one magnet that magnetically couples the main body to the nut; and opposed barrier blocks within the main body, wherein the opposed barrier blocks define a blade slot therebetween, wherein the blade slot has a clearance height that is greater than a depth of the cutting blade, wherein the blade slot connects to the nut-retention chamber, wherein the cutting blade is configured to pass into the blade slot and be secured within a blade chamber that is longer, wider, and deeper than the cutting blade, wherein the main body is configured to suspend the cutting blade within the blade chamber, wherein no portion of the cutting blade directly contacts any portion of the blade-protecting sheath when the cutting blade is secured within the blade chamber.

* * * * *